United States Patent [19]
Hewitt et al.

[11] Patent Number: 5,216,759
[45] Date of Patent: Jun. 8, 1993

[54] SAFETY GOGGLES LENS RETENTION

[75] Inventors: Charles D. Hewitt, North Tonawanda; Andrew T. Kelley, Buffalo, both of N.Y.

[73] Assignee: American Allsafe Company, Tonawanda, N.Y.

[21] Appl. No.: 867,752

[22] Filed: Apr. 13, 1992

[51] Int. Cl.⁵ .............................. A61F 9/02
[52] U.S. Cl. ............................. 2/439; 2/431
[58] Field of Search ............ 2/439, 447, 431, 426, 2/429, 440, 441, 442, 443, 444; 277/50, 189; 351/83, 86, 47, 178

[56] References Cited

U.S. PATENT DOCUMENTS

| | | |
|---|---|---|
| 1,471,562 | 10/1923 | Malcom . |
| 1,565,890 | 12/1925 | Baker . |
| 1,573,088 | 2/1926 | Peloquin . |
| 1,584,259 | 5/1926 | Tully . |
| 2,342,766 | 2/1944 | Stiano . |
| 2,364,584 | 12/1944 | Malcom . |
| 2,387,851 | 10/1945 | Lown et al. . |
| 2,533,547 | 12/1950 | Anderson . |
| 2,648,843 | 8/1953 | Hirschmann . |
| 2,706,815 | 4/1955 | Parmelee . |
| 2,715,223 | 8/1955 | Stegeman et al. . |
| 2,846,684 | 8/1958 | Hill . |
| 2,895,138 | 7/1959 | Miller . |
| 2,981,957 | 5/1961 | Hirschmann . |
| 3,000,011 | 9/1961 | Sterne et al. . |
| 3,031,674 | 5/1962 | Ring . |
| 3,122,962 | 3/1964 | DeAngelis . |
| 3,141,172 | 7/1964 | Hirschmann . |
| 3,259,909 | 7/1966 | Wood . |
| 3,409,909 | 11/1968 | Scott et al. . |
| 3,444,561 | 5/1969 | Boyer .................... 2/8 |
| 3,638,240 | 2/1972 | Militello . |
| 3,708,224 | 1/1973 | Lindblom . |
| 3,924,271 | 12/1975 | Hirschmann, Jr. . |
| 4,264,988 | 5/1981 | Secht .................... 2/431 |
| 4,447,914 | 5/1984 | Jannard ................. 2/432 |
| 4,455,688 | 6/1984 | Poe ...................... 2/431 |
| 4,707,863 | 11/1987 | McNeal ................. 2/436 |
| 4,709,696 | 12/1987 | Angell . |
| 4,796,308 | 1/1989 | Bourgeois ............. 2/243 |

FOREIGN PATENT DOCUMENTS

| | | | |
|---|---|---|---|
| 509513 | 1/1955 | Canada ................. 2/447 |
| 1460014 | 11/1966 | France ................. 2/447 |

Primary Examiner—Clifford D. Crowder
Assistant Examiner—Michael A. Neas
Attorney, Agent, or Firm—Dennis T. Griggs

[57] ABSTRACT

The eye protection lens of safety goggles provides increased impact protection without utilizing external fasteners or external sealing means. The mechanical attachment of the lens to the goggles rim is improved and stabilized against separation forces by the interlocking engagement of a wedge shaped retainer rib formed along the periphery of the safety lens. The lens support frame has a retainer rim which is intersected by an open slot, thereby defining an outside body portion and an inside body portion. An annular shoulder is formed on the inside body portion and partially closes the open slot. The retainer rib is received within the slot, with its apex being engaged against the inside body portion of the goggles rim, and the wedge portion of the retainer rib being disposed in overlapping, interlocking engagement with the annular shoulder.

5 Claims, 2 Drawing Sheets

SAFETY GOGGLES LENS RETENTION

FIELD OF THE INVENTION

This invention relates generally to personal safety equipment, and in particular to safety goggles intended for industrial use.

BACKGROUND OF THE INVENTION

A conventional form of safety goggles in widespread use include a plastic safety lens which extends across both eyes of the wearer and which is enclosed within a flexible, plastic frame which wraps around the lens along its front edge and extends rearwardly and is shaped to fit the face of the wearer along its rear edge. The frame and lens thus combine to form an enclosed space in front of the wearer's eyes and the surrounding portions of his face. Goggles of this general type are shown in U.S. Pat. No. 3,638,240, assigned to American Allsafe Company, Inc.

Safety goggles provide limited protection against eye injuries which might be caused by hazardous working conditions. Safety goggles are sometimes worn in combination with a hard hat and include an elastic strap which holds the goggles securely about the wearer's head. The purpose of the goggles is to protect the eyes against the impact of flying materials, and also to shield the eyes from exposure to chemical splash and the like.

DESCRIPTION OF THE PRIOR ART

Single-aperture, single lens safety goggles are in widespread use. Typically, the goggles include a frame which is molded of a relatively soft, flexible plastic material, and a separately fabricated plastic lens having a convex curvature. Generally, such goggles are simple in construction and are relatively inexpensive to manufacture, while providing eye protection under hazardous working conditions. The goggles should be lightweight, easy to wear and comfortable. Goggles which are heavy, awkward and uncomfortable are not likely to be used, thereby defeating their purpose.

In an effort to simplify the construction of safety goggles, the goggles frame and the safety lens are separately fabricated, and the safety lens is attached to the goggles frame during final assembly. Various means are used to secure the lens to the goggles frame, including interlocking male/female snap fasteners, adhesive deposits, screw fasteners, and interlocking flange members.

According to one simple interlocking arrangement, the peripheral edge of the lens is received within a retainer slot formed along the forward rim of the goggles frame. The outside edge of the lens is confined within the groove between parallel flange portions which are separated by the slot. According to that arrangement, external fasteners are not utilized, with the lens being retained by compressive engagement of the goggles frame and by the confining action of the flange portions. The mechanical union of the lens against the frame also provides a secure, fluid seal.

A limitation on the use of safety goggles having lens slot retention is the tendency of the inner flange portion of the goggles frame to deflect in response to a high impact force applied to the lens. Deflection of the lens relative to the goggles frame may be severe enough to interrupt the seal along the lens/frame interface, with the result that the wearer's eyes may then be exposed to contact by chemical splash.

OBJECTS OF THE INVENTION

In view of the foregoing limitations on goggles having conventional safety lens retention, there is a continuing interest in improving the integrity of the fluid seal and the mechanical attachment of the safety lens to the goggles rim.

Accordingly, the principal object of the present invention is to provide an improved lens retention arrangement for safety goggles with increased impact protection, but without utilizing external fasteners or external sealing means.

A related object of the present invention is to provide an improved lens retention arrangement for safety goggles of the character described, in which the mechanical attachment of the lens to the goggles rim is improved and stabilized against separation forces.

Another object of the present invention is to provide an improved lens retention arrangement for safety goggles of the character described, in which the lens is relatively easily insertable into interlocking engagement with the goggles rim, with the force required to produce separation of the lens from interlocking engagement being substantially greater than the force required to complete insertion.

A related object of the present invention is to provide an improved lens retention arrangement for safety goggles of the character described, in which the lens and goggles frame are modified to provide interlocking engagement which opposes release and separation of the lens from the frame.

Still another object of the present invention is to provide an improved lens retention arrangement of the character described, in which the engaging portion of the lens is modified to enhance sealing engagement with the goggles rim in response to a pressure differential applied across the lens.

SUMMARY OF THE INVENTION

The foregoing objects are provided by safety goggles of the type having an eye protection lens of transparent material received within an annular slot formed in the lens retainer rim portion of a unitary goggles frame. According to the preferred embodiment, the retainer rim is intersected by an open slot, and the eye protection lens has a marginal edge portion received within the slot. The marginal edge portion of the lens has a retainer lip which projects transversely with respect to the eye protection lens and is engaged against the retainer rim.

According to one aspect of the invention, the retainer lip has an outside body portion and an inside body portion separated by the slot, and the retainer lip has a wedge portion formed by first and second faces which converge and intersect along an apex. The apex is engaged against the inside body portion of the retainer lip.

According to another aspect of the invention, an annular shoulder is formed on the inside body portion of the lens retainer rim, and the annular shoulder partially closes the open slot. The retainer rib of the eye protection lens has first and second transversely disposed faces which intersect along an apex. The apex is engaged against the inside body portion of the retainer rim, and the wedge portion is disposed in overlapping, interlocking engagement with the annular shoulder.

According to the preferred embodiment of the invention, engagement of the rib against the retainer rim improves the integrity of the fluid seal and the mechanical attachment of the safety lens to the goggles rim to protect against the impact of hazardous materials. That is, the mechanical attachment of the lens to the goggles rim is improved and stabilized against separation forces, without using external fasteners or external sealing means.

BRIEF DESCRIPTION OF THE DRAWINGS

Operational features and advantages of the present invention will be understood by those skilled in the art upon reading the detailed description which follows with reference to the attached drawings, wherein.

DETAILED DESCRIPTION OF THE PREFERRED EMBODIMENT

Figure 1:
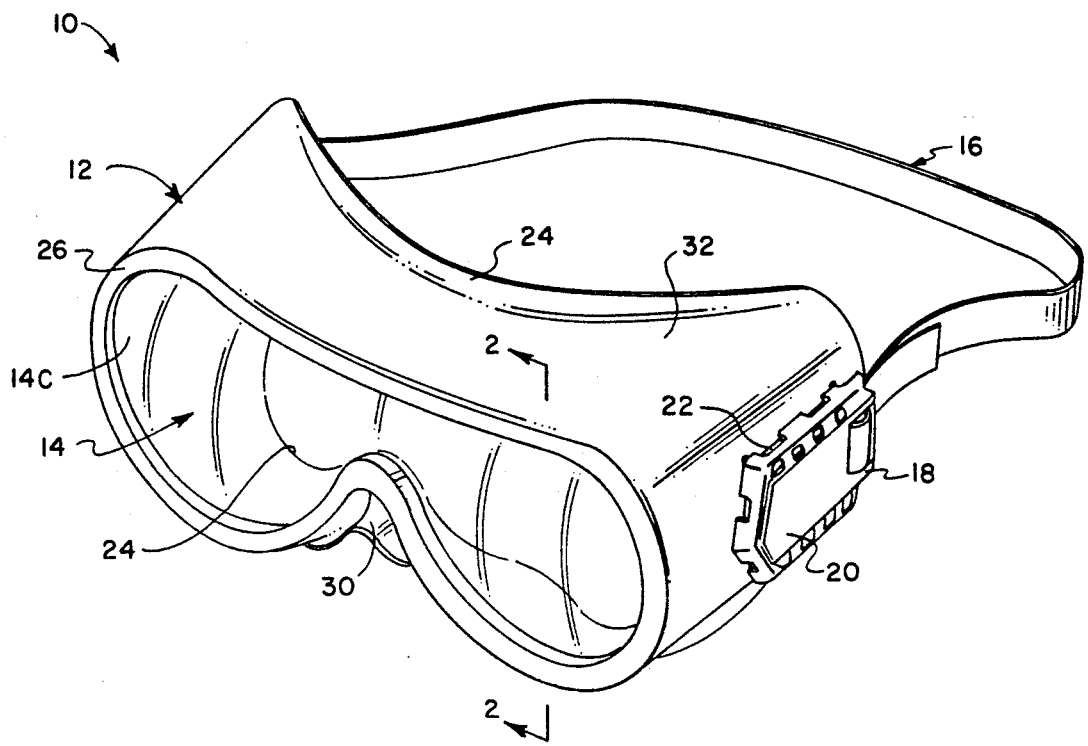
FIG. 1 is a perspective view of a safety goggles having a lens retention arrangement constructed according to the teachings of the present invention.

In the description which follows, like parts are indicated throughout the specification and drawings with the same reference numerals, respectively. The drawings are not necessarily to scale and the proportions of certain parts have been exaggerated for better illustration of construction details.

Safety goggles 10 constructed according to the preferred embodiment of the present invention has three principal components, namely an integral frame 12, an eye protection lens 14 and an elastic head strap 16. The head strap 16 is in the form of a continuous strap which extends from one side of the goggles frame to the other side. The ends of the head strap 16 are releasably attached to the goggles frame 12 by a bracket fastener 18. The bracket fastener overlies a vent opening (not shown), which is covered by a protective vent plate 20. Ventilation ports 22 are formed in the vent plate for permitting the circulation of ambient air into the space enclosed by the goggles frame 12.

The goggles frame 12 is constructed of a relatively soft, impervious, resilient plastic material which allows the facial contour portions 24 to readily conform to the contour of the individual wearer. The material is preferably a moldable plastic material such as flexible polyvinyl chloride (PVC) and the like.

The eye protection lens 14 may be made of any transparent, high impact resistant material such as polycarbonate, which can be then coated with anti-fogging and/or scratch resistant coatings. The lens may also be treated to reduce the transmission of ultraviolet (UV), infrared (IR) and laser light. Preferably, the eye protection lens 14 is formed generally in a double ovate orbicular outline.

The goggles frame 12 has a forward lens retainer rim which circumscribes a viewing window 28. The facial contour portion 24 is contoured to conform to the face of the wearer around the eyes and across the nose, and includes a flexible bridge portion 30 which rides on the wearer's nose. The lens retainer rim 26 and the facial contour portion 24 are joined by a protective sidewall 32 which projects rearwardly from the retainer rim 26.

The protective sidewall 32 is continuously and integrally formed so as to provide a protective covering enclosure immediately in front of the wearer's eyes.

The eye protection lens 14 has a main lens body portion 14A of convex curvature, and a marginal edge portion 14B which is adapted for insertion into an annular slot 34 formed in the lens retainer rim 26. The lens retainer rim 26 has a body portion 26A which is intersected by the slot 34. The slot 34 is an open, continuous slot which is formed as the goggles frame 12 is molded.

According to this arrangement, the retainer rim body portion 26A is bifurcated by the annular slot 34. The annular slot 34 thus separates an outside body portion 26B and an inside body portion 26C.

Figure 2:
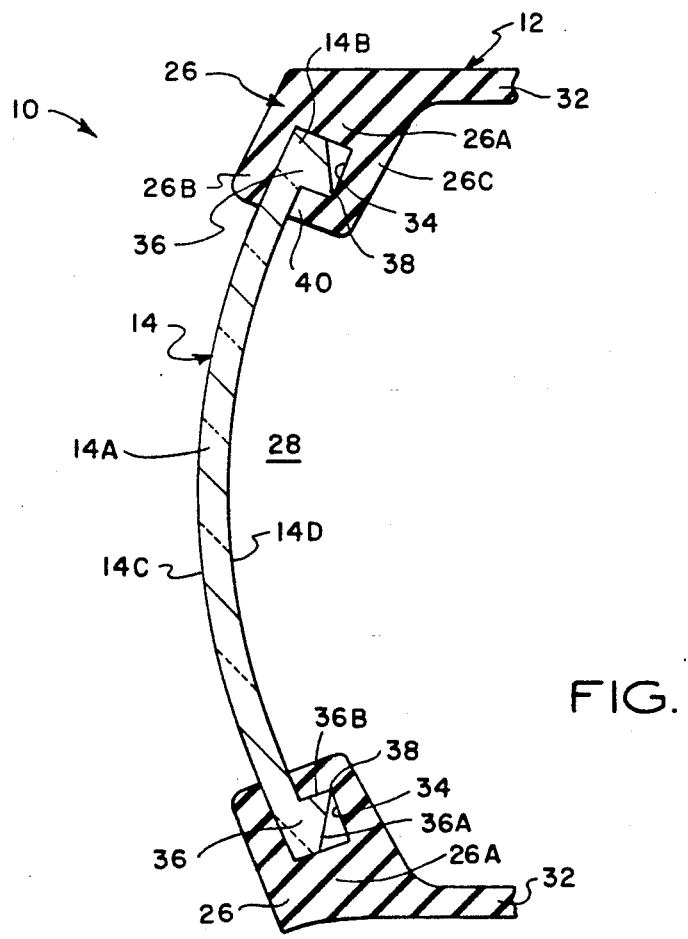
FIG. 2 is a sectional view, partially broken away, taken along the line 2—2 of FIG. 1.

The marginal edge portion 14B of the eye protection lens 14 is substantially complementary to the shape of the lens retainer rim 26, and is dimensioned to provide a snug, interference fit upon full insertion into the slot 34, as shown in FIG. 2. According to one aspect of the present invention, the marginal edge portion 14B of the lens has a rib 36 formed along its inside peripheral edge. The rib 36 projects transversely with respect to the lens, and engages the body 26A of the lens retainer rim.

Preferably, the rib is in the form of a lip or wedge having an apex 38 engaging against the inside body portion 26C of the retainer rim. The rib 36 and the annular slot 34 are dimensioned to provide a snug, interference fit with the apex 38 of the retainer rib being engaged against the inside retainer rim body portion 26C.

Figure 3:
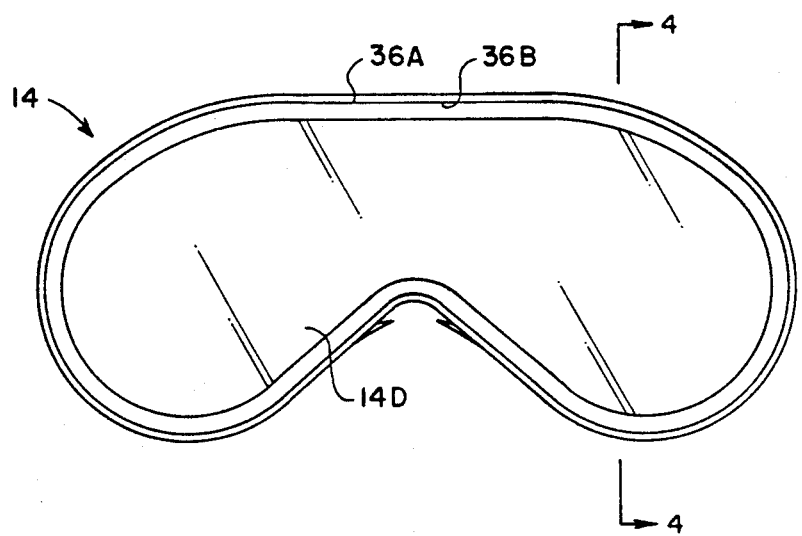
FIG. 3 is a front elevational view of the safety lens shown in FIG. 1.
Figure 4:
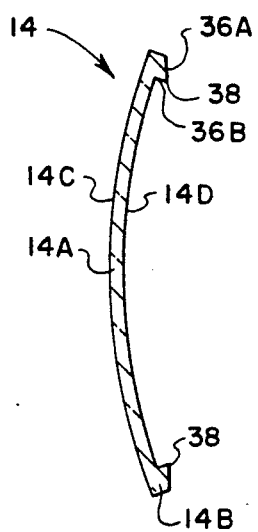
FIG. 4 is a sectional view thereof, taken along the line 4—4 of FIG. 3.
Figure 5:
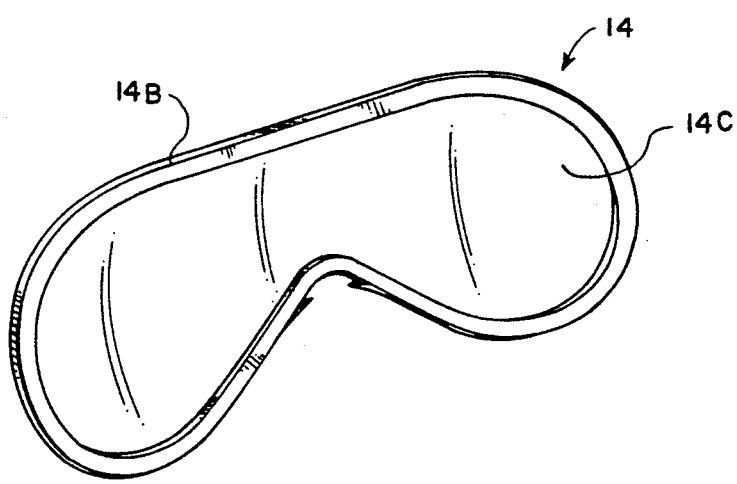
FIG. 5 is a rear perspective view of the safety lens shown in FIG. 1.

Referring now to FIG. 2, FIG. 3 and FIG. 4, the retainer rib 36 has faces 36A, 36B which project transversely with respect to the lens body 14A and converge along the apex 38. As can best be seen in FIG. 2, the retainer rib 36 is wedge shaped in profile, and projects transversely with respect to the marginal edge portion 14B of the eye protection lens 14. The converging faces 36A, 36B and the apex 38 extend continuously around the periphery of the eye protection lens 14, thereby providing continuous, sealing engagement against the body portion 26A of the lens retainer rim.

According to another aspect of the present invention, a continuous shoulder 40 is formed on the inside body portion 26C, thereby partially closing the open retainer slot 34. In this arrangement, the lower face 36B of the wedge 36 is engaged in overlapping, interlocking union with the shoulder 40. At the same time, the apex 38 is held under compression between the outside body portion 26B and the inside body portion 26C, with the continuous apex 38 providing a fluid seal at the point of engagement.

Moreover, the outside body portion 26B and inside body portion 26C engage opposite side surfaces 14C, 14D of the lens when the marginal edge portion 14B of the lens is fully inserted within the annular slot. The outside lens surface 14C is exposed, and the inside lens surface 14D is protected by the goggles frame 12. According to this arrangement, external fasteners are not utilized, with the eye protection lens 14 being retained by compressive engagement of the retainer rim 26 and by the confining action of the interlocking engagement of the wedge 36 with the lens retainer rim shoulder portion 40.

Because the body 26A of the retainer rim 26 is yieldable, the peripheral edge portion 14B of the eye protection lens 14 is easily insertable into the open slot 34, with the sloping wedge surface 36A providing a ramp for facilitating insertion. However, because of the interlocking engagement of the shoulder 40 and wedge shaped retainer rib 36, a substantially greater force is required to produce separation of the lens from interlocking engagement and withdrawal of the marginal edge portion from the retainer slot 34. That is, the outside body portion 26B and inside body portion 26C yield and deflect to permit insertion of the retainer rib 36, but the interlocking engagement of the shoulder 40 against the rib 36 opposes release and separation of the lens 14 from the frame 12.

It will be appreciated that the interlocking engagement of the wedge shaped rib with the retainer rim improves the integrity of the fluid seal and stabilizes the mechanical attachment of the safety lens to the goggles rim. The eye protection lens 14 will be securely retained and sealed against the retainer rim 26 for increased impact protection. Differential pressure applied across the lens relative to the frame tends to intensify the force of engagement of the apex against the rim body, thereby enhancing the fluid seal, and opposing lens separation which would interrupt the seal and expose the wearer's eyes to contact by chemical splash liquids.

Although the invention has been described in part by making detailed references to certain specific embodiments, such detail is intended to be, and will be understood to be, instructional rather than restrictive. Accordingly, it is intended that all matter contained in the drawings and specification shall be interpreted as illustrative and not in a limiting sense.

What is claimed is:

1. Safety goggles comprising, in combination:
    an eye protection lens of transparent material, said lens having a marginal edge portion extending around the periphery thereof;
    a lens support frame having a lens retainer rim circumscribing a viewing window and a protective sidewall projecting rearwardly from the retainer rim, said frame being formed of a flexible, relatively soft material, contoured to conform to the face of the wearer around the eyes and across the nose, said retainer rim having a body portion intersected by an open slot thereby defining an outside body portion and an inside body portion separated by said slot, the outside body portion and the inside body portion engaging opposite side surfaces of said lens when the marginal edge portion of said lens is fully inserted into said slot; and,
    the marginal edge portion of said lens having a rib received within said slot, said rib projecting transversely with respect to said lens and extending around the entire marginal edge portion, said rib including a wedge portion having an apex disposed in engagement against the inside body portion of said retainer rim.

2. Safety goggles as defined in claim 1, the inside body portion of said retainer rim having a shoulder projecting transversely with respect to the inside body portion and partially closing said open slot, said shoulder engaging the inside surface of the eye protection lens, and said rib engaging said shoulder when the marginal edge portion of the eye protection lens is fully inserted into an open slot.

3. Safety goggles as defined in claim 1, said rib having first and second faces extending transversely with respect to said lens and intersecting along a continuous apex, said apex engaging the inside body portion of said retainer rim.

4. Safety goggles comprising a unitary, molded frame having a lens retainer rim circumscribing a viewing window, said retainer rim being intersected by an open slot, thereby defining an outside body portion and an inside body portion separated by said slot, and an eye protection lens of transparent material having a marginal edge portion received within said slot, the marginal edge portion of said lens having a retainer lip projecting transversely with respect to the eye protection lens and extending around the entire marginal edge portion, said retainer lip including a wedge portion having first and second faces which converge and intersect along an apex, said apex being disposed in engagement against the inside body portion of said retainer lip.

5. In safety goggles of the type including a lens and molded frame having a lens retainer rim circumscribing a viewing window, and said rim having a body portion intersected by an open slot thereby defining an outside body portion and an inside body portion separated by said slot, with the outside body portion and inside body portion engaging opposite sides of said lens when the marginal edge portion of said lens is fully inserted into said slot, the improvement comprising:
    a shoulder formed on the inside body portion and projecting transversely with respect to the inside body portion, said shoulder partially closing said open slot; and,
    the marginal edge portion of said lens having a rib received within said slot, said rib having a wedge portion bounded by first and second faces extending transversely with respect to said eye protection lens and converging along an apex, said apex being disposed in engagement against the inside body portion of said retainer rim, and said wedge portion being disposed in overlapping, interlocking engagement with said shoulder.

* * * * *

UNITED STATES PATENT AND TRADEMARK OFFICE
CERTIFICATE OF CORRECTION

PATENT NO.    : 5,216,759
DATED         : June 8, 1993
INVENTOR(S)   : Charles D. Hewitt/Andrew T. Kelley It is certified that error appears in the above-identified patent and that said Letters Patent is hereby corrected as shown below:

Column 4, line 32, "Which" should be -- which --.

Signed and Sealed this

Fourth Day of January, 1994

Attest:

BRUCE LEHMAN

Attesting Officer        Commissioner of Patents and Trademarks